(12) United States Patent
Koh et al.

(10) Patent No.: US 7,519,426 B1
(45) Date of Patent: Apr. 14, 2009

(54) TECHNIQUES FOR REDUCING ORTHOSTATIC HYPOTENSION

(75) Inventors: Steve Koh, South Pasadena, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 624 days.

(21) Appl. No.: 11/245,875

(22) Filed: Oct. 7, 2005

(51) Int. Cl.
*A61N 1/18* (2006.01)
(52) U.S. Cl. .......................................................... 607/42
(58) Field of Classification Search ....................... 607/9
See application file for complete search history.

(56) References Cited

U.S. PATENT DOCUMENTS

| | | | |
|---|---|---|---|
| 5,476,483 A | 12/1995 | Bornzin et al. | 607/17 |
| 6,662,047 B2 | 12/2003 | Sorensen et al. | 607/18 |
| 6,738,666 B1 | 5/2004 | Park et al. | 607/18 |
| 7,363,085 B1 * | 4/2008 | Benser et al. | 607/42 |

OTHER PUBLICATIONS

Yates, B.J., et al. "Vestibular Effects on Respiratory Outflow in the Decerebrate Cat," *Brain Research*, 1993; vol. 629, pp. 209-217.

* cited by examiner

*Primary Examiner*—Carl H. Layno
*Assistant Examiner*—Jon-Eric Morales

(57) ABSTRACT

Techniques for reducing orthostatic hypotension are described. One technique detects an incident of orthostatic hypotension in a patient, and in response, increases cardiac stroke volume, at least in part, by stimulating the patient's phrenic nerve.

18 Claims, 4 Drawing Sheets

TECHNIQUES FOR REDUCING ORTHOSTATIC HYPOTENSION

FIELD OF THE INVENTION

Subject matter presented herein generally relates to methods and systems for providing cardiac pacing therapy. More particularly, the subject matter concerns methods and implantable stimulation devices to detect onset of orthostatic hypotension and/or to reduce and/or eliminate orthostatic hypotension.

BACKGROUND

Orthostatic hypotension (OSH) is a common geriatric disorder as well as a common side effect of many medications. It is generally described as a decrease of 10-20 millimeters of mercury (mmHg) or more in systolic blood pressure when posture changes from supine to standing-a horizontal to vertical change in posture. OSH can have neurogenic etiologies (e.g., diminished baroreceptor reflex); vestibular disorders; peripheral/central nervous system deficiencies; etc.) or non-neurogenic etiologies (e.g., cardiac pump failure, reduced blood volume, venous pooling, etc.).

When a patient's natural ability to prevent or minimize incidences of OSH become less effective, there remains a need for effective techniques that anticipate OSH and take actions to reduce the severity of OSH that may occur and/or eliminate the occurrence of OSH.

SUMMARY

Techniques for reducing or eliminating orthostatic hypotension are described. One technique detects an incident of orthostatic hypotension in a patient and in response, increases cardiac stroke volume, at least in part, by stimulating the patient's phrenic nerve.

DETAILED DESCRIPTION

Overview

Figure 1:
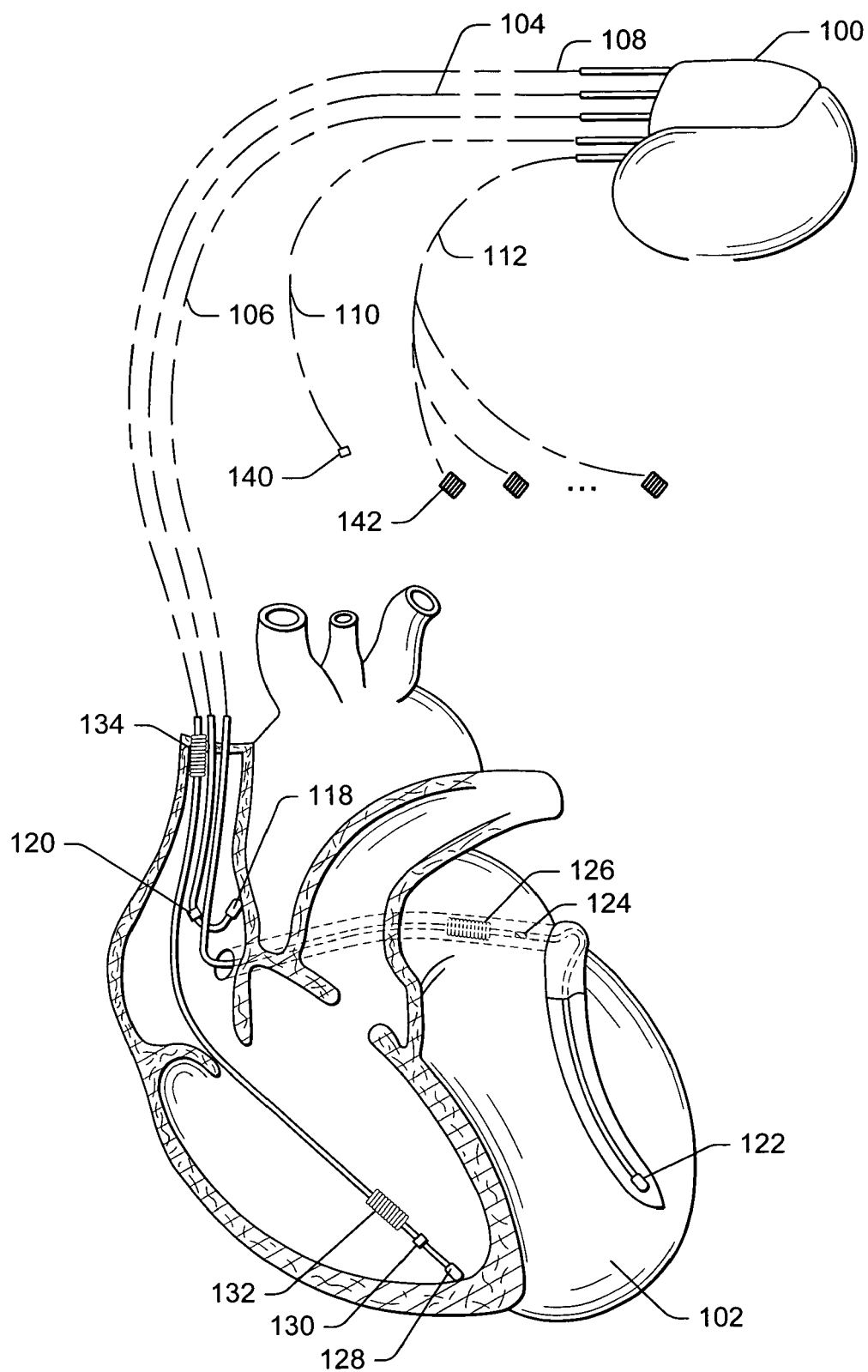
FIG. 1 is a diagram illustrating an exemplary implantable device in electrical communication with a human heart and configured to reduce orthostatic hypotension in accordance with one implementation.

The following discussion describes an exemplary implantable device ("device") that includes a responsive cardiovascular controller. The device exerts artificial diaphragm control and artificial cardiac control. The device also receives information from one or more physiological sensors and adjusts one or both of the artificial diaphragm control and the artificial cardiac control based on the physiological information.

In one implementation, the device is capable of detecting a patient condition which may be indicative of orthostatic hypotension or impending orthostatic hypotension. Examples of such patient conditions can include changes in postures, changes in blood pressure, and changes in activity level, among others.

Responsive to detecting one or more patient conditions, the device is configured to cause a decrease in the patient's intra-thoracic pressure. A decrease in the patient's intra-thoracic pressure allows increased cardiac stroke volume, which can serve to increase cardiac output to positively affect the patient's blood pressure.

In some instances, the device is capable of increasing cardiac stroke volume, at least in part, by decreasing intra-thoracic pressure. For instance, the device is capable of stimulating diaphragm activation, which produces decreased intra-thoracic pressure to reduce intrinsic pressure on the heart. Decreasing pressure on the heart allows greater volumetric expansion of the heart. This results in a relatively higher refill volume, translating to greater cardiac stroke volume.

In one instance, the device is configured to stimulate the patient's phrenic nerve which in turn stimulates the diaphragm. In another implementation, the device is configured to stimulate more directly the tissues of the diaphragm.

In addition to stimulating the diaphragm, the device may be configured to concurrently increase a rate of cardiac pacing from an existing pacing rate. The increased pacing rate, in combination with the increased stroke volume, positively affects the patient's blood pressure by increasing the patient's cardiac output.

Beyond sensing capabilities, such as those described above, the device may also contain feedback control mechanisms to coordinate the device's various activities. For instance, responsive to taking one or more actions as described above, the device may be capable of receiving blood pressure samples and comparing those samples to a pre-established maximum blood pressure value. This feedback control ensures that the various actions taken to positively affect the patient's blood pressure do not overcompensate to undesirably high blood pressures values.

In this document, the term "orthostatic hypotension incident" or "OSH incident" is intended to include scenarios in which sensed parameters from the patient indicate OSH is occurring as well as scenarios in which sensed parameters from the patient indicate an imminent onset of OSH. For example, an OSH incident includes a scenario where the patient moves from a generally supine position to a generally upright position and experiences an accompanying drop in blood pressure sufficient to be classified as OSH. Another example of an OSH incident occurs when the patient is in the process of moving from the prone position to the generally upright position and begins to experience decreasing blood pressure, but where intervening action is taken such that the patient's blood pressure does not drop to levels which would generally be defined as OSH.

Exemplary Implantable Device

FIG. 1 shows an exemplary implementation of an implantable device 100 introduced above in electrical communication with a human heart 102 and other bodily tissues. Such an exemplary device 100 can be characterized as a miniature computing device that is implanted into a patient's body to monitor, regulate, and/or correct cardiovascular and other activities. The device 100 may be an ICD (e.g., implantable cardiac pacemaker, implantable defibrillator, etc.) that applies stimulation therapy to the heart or may be another type of implantable device that can perform the responsive diaphragm activation techniques described herein.

While a single device in described in relation to FIG. 1, other devices may include multiple components configured to cooperatively achieve a desired functionality. Further, some devices and/or sub-components of a device may be configured to operate externally. For instance, an external device for diaphragm activation may communicate with an implanted device (e.g., an implanted cardiac therapy device, etc.).

In the illustrated implementation, three of the electrical leads—a right atrial lead 104, a coronary sinus lead 106, and a right ventricular lead 108—interconnect the device 100 with the heart 102 to support multi-chamber detection and stimulation therapy. One or more physiological sensor lead(s) 110 may also be employed to position physiological sensors within the body and a diaphragm activation lead 112 may be used to position electrodes to facilitate stimulation of the diaphragm, such as by stimulating the phrenic nerve at one or more locations.

The right atrial lead 104 supports an atrial tip electrode 118, which is typically implanted in a patient's right atrial appendage. The right atrial lead 104 also supports a right atrial ring electrode 120, which enables the device to sense atrial cardiac signals and apply pacing therapy to the right atrial chamber. The lead 104 may have other electrodes in addition to those shown in FIG. 1. For example, the right atrial lead 104 may optionally include a distal bifurcation having electrodes suitable for stimulation of the phrenic nerves.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the implantable device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed to apply left atrial pacing therapy, and the left atrial coil electrode 126 may be used for shocking therapy. The coronary sinus lead 106 optionally includes electrodes for stimulation of phrenic nerves. Such a lead may include cardiac pacing functionality and phrenic nerve stimulation functionality and may further include bifurcations or branches to reach the target tissues. For example, an exemplary coronary sinus lead includes pacing electrodes capable of delivering pacing pulses to a patient's left ventricle and at least one electrode capable of stimulating a phrenic nerve. Such an electrode may be positioned on the lead or a bifurcation or leg of the lead.

The right ventricular lead 108 is electrically coupled to a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle. An exemplary right ventricular lead may also include at least one electrode capable of stimulating a phrenic nerve; such an electrode may be positioned on the lead or a bifurcation or leg of the lead. For example, an exemplary right ventricular lead includes pacing electrodes capable of delivering pacing pulses to a patient's left ventricle and at least one electrode capable of stimulating the phrenic nerve.

One or more physiological sensor lead(s) 110 position one or more physiological sensors 140 in various positions in the human body to sense physiological parameters that may be used in diagnosing the patient's condition and controlling responsive stimulation therapy. One example of physiological sensor 140 is a blood pressure probe, such as a photoplethysmograph (PPG) infrared light sensor, which is placed in contact with the patient's blood to sense blood pressure. Alternatively or additionally, physiological sensor 140 may be utilized to sense intrinsic or native neural stimulation of the phrenic nerve by the central nervous system.

Diaphragm activation lead 112 is positioned in the patient to facilitate stimulation of the phrenic nerve in one or more places to cause contraction of the diaphragm. In one configuration, one or more cuff electrodes 142 are used to couple the diaphragm activation lead 112 to nerve tissue.

Figure 2:
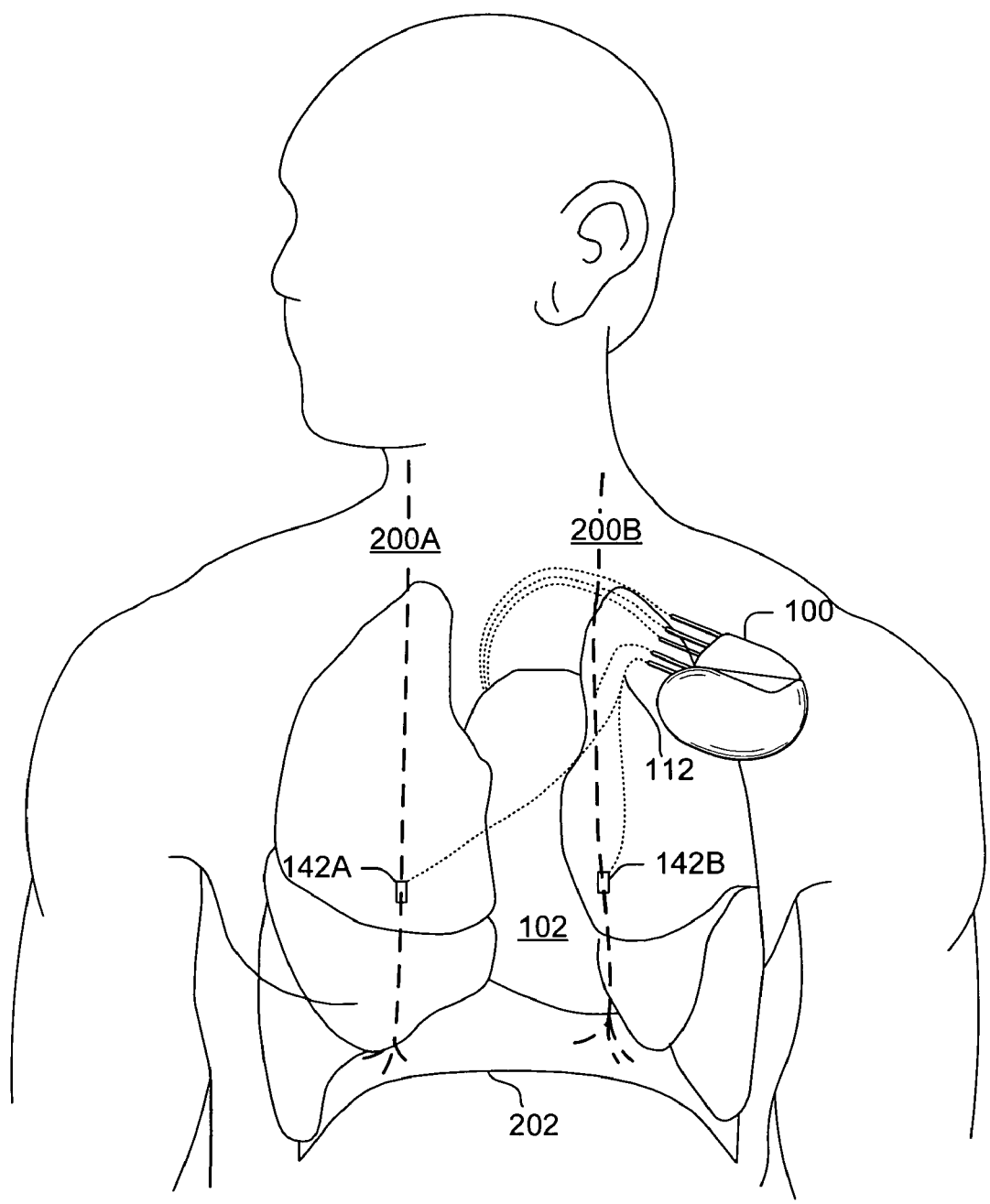
FIG. 2 is a diagram illustrating the exemplary implantable device in relation to a human body in accordance with one implementation.

FIG. 2 shows an exemplary configuration for achieving diaphragm activation responsive to an OSH incident, where implantable device 100 is coupled to stimulate the patient's phrenic nerve. In general, phrenic nerves 200A and 200B run from above the subclavian veins and down around the heart 102 (e.g., left and right side) to the surface of diaphragm 202. Diaphragm activation lead 112 couples the device 100 to the phrenic nerves through placement of a first cuff electrode 142A on the right phrenic nerve 200A and a second cuff electrode 142B on the left phrenic nerve 200B. An electrical charge can be delivered to the phrenic nerve(s) via one or both cuff electrodes to achieve activation of diaphragm 202.

While a specific phrenic nerve stimulation configuration is illustrated here, many other configurations are possible. For instance, direct phrenic nerve stimulation uses one or more electrodes or poles (e.g., magnetic stimulation) in close proximity (e.g., typically in contact with) to a phrenic nerve. Such electrodes or poles may be positioned in the cervical region or other regions of the phrenic nerves which may be superior to the heart, proximate to the heart, and/or inferior to the heart, noting that such positioning and/or stimulating may consider risk of parasitic or inadvertent cardiac activation.

Alternatively or additionally to stimulating the phrenic nerve utilizing a dedicated lead, such as diaphragm activation lead 112, phrenic nerve stimulation can be achieved via a branch off of one or more of the cardiac stimulation leads. Examples of such leads can include a right atrial lead 104, a coronary sinus lead 106, and a right ventricular lead 108 as designated above in FIG. 1. Transvenous phrenic nerve stimulation involves positioning one or more electrodes or poles in a vessel proximate to a phrenic nerve. For example, the right phrenic nerve runs along the intimal tissue of the superior vena cava and the left phrenic nerve runs near the innominate vein.

Some implementations may more directly stimulate the diaphragm or either or both of the diaphragms two hemidiaphragms. Stimulation of the diaphragm from one or more electrodes or poles positioned proximate to or in the diaphragm may achieve diaphragm activation and resultant decreases in intra-thoracic pressure suitable for reducing OSH. In one example, a pair of electrodes is positioned intramuscularly proximate to the region where a phrenic nerve innervates a hemidiaphragm. In this example, stimulation delivered via the pair of electrodes causes diaphragm activation via nerve and/or muscle excitation. Further, another implantable device, configured to operate cooperatively with device 100 and capable of delivering stimulation for diaphragm activation, may be placed subcutaneously in or near the abdomen in a manner that is less invasive than that associated with a pectoral pocket implant.

Figure 3:
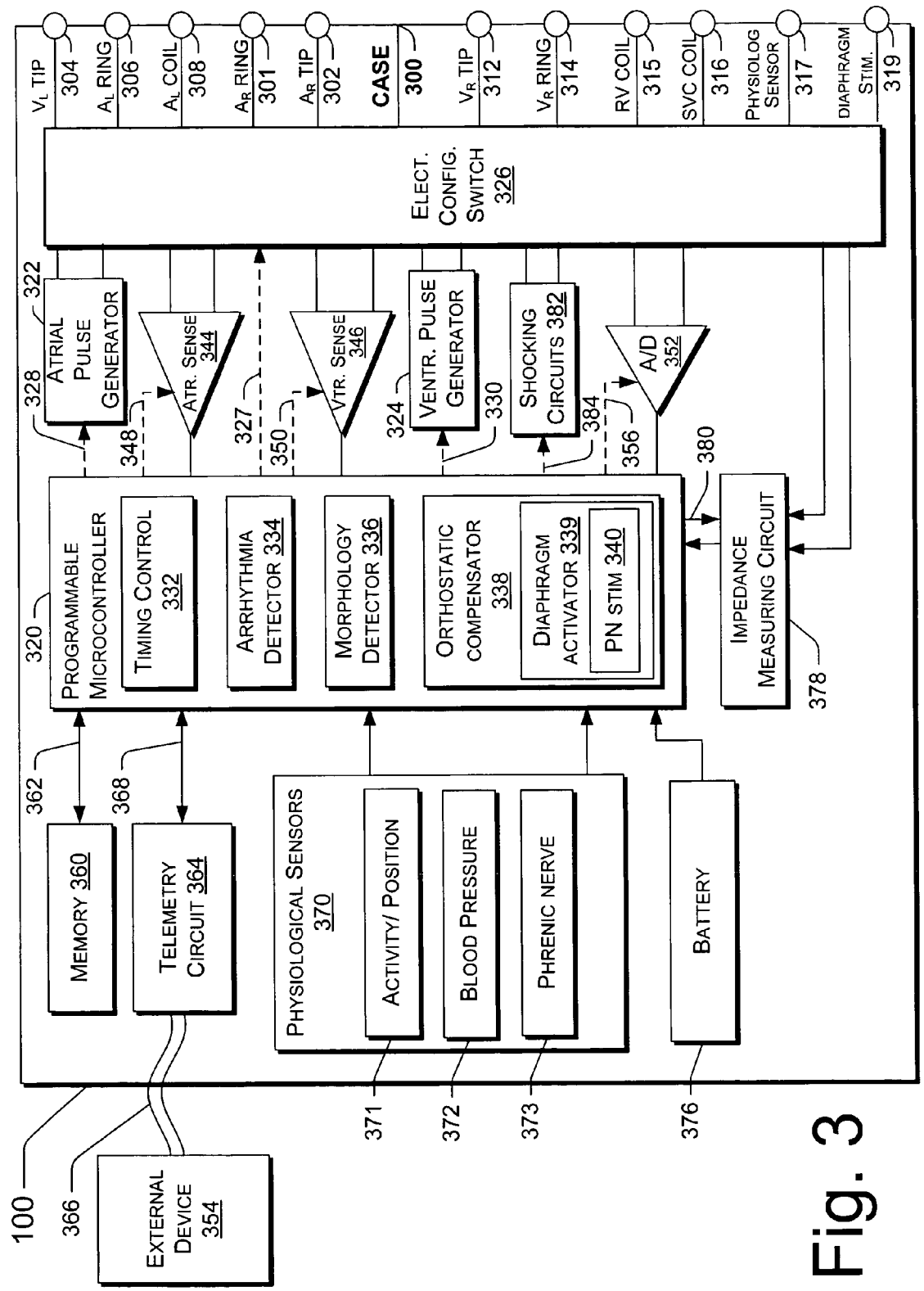
FIG. 3 is block diagram of an exemplary implementation of an implantable device.

FIG. 3 shows various functional components of the implantable device 100. The components are typically contained in a case 300, which is often referred to as the "can", "housing", "encasing", or "case electrode", and may be programmably selected to act as the return electrode for unipolar operational modes. The case 300 may further be used as a return electrode alone, or in combination with, one or more of the coil electrodes 126, 132 and 134 (as described above in relation to FIG. 1) for stimulating purposes. The case 300 further includes a connector (not shown) having a plurality of terminals (301, 302, 304, 306, 308, 312, 314, 315, 316, 317, and 319—shown schematically with the names of the electrodes to which they are connected shown next to the terminals), including:

- a right atrial ring terminal ($A_R$ RING) 301 for atrial ring electrode 120;
- a right atrial tip terminal ($A_R$ TIP) 302 for atrial tip electrode 118;
- a left ventricular tip terminal ($V_L$ TIP) 304 for left ventricular tip electrode 122;
- a left atrial ring terminal ($A_L$ RING) 306 for left atrial ring electrode 124;
- a left atrial shocking terminal ($A_L$ COIL) 308 for left atrial coil electrode 126;
- a right ventricular tip terminal ($V_R$ TIP) 312 for right ventricular tip electrode 128;
- a right ventricular ring terminal ($V_R$ RING) 314 for right ventricular ring electrode 130;
- a right ventricular shocking terminal (RV COIL) 315 for RV coil electrode 132;
- an SVC shocking terminal (SVC COIL) 316 for SVC coil electrode 134;
- a physiological sensor terminal 317 for physiological sensor 140, e.g., a blood pressure probe; and
- a diaphragm stimulation terminal 319 for coupling with a diaphragm activation lead 112 and/or for coupling with one or more of the right atrial lead 104, coronary sinus lead 106, and right ventricular lead 108 as mentioned above in relation to FIG. 1.

An exemplary device 100 may include a programmable microcontroller 320 that controls various operations of the implantable cardiac device, including cardiac monitoring and cardiovascular stimulation therapy. Microcontroller 320 includes a microprocessor (or equivalent control circuitry), RAM and/or ROM memory, logic and timing circuitry, state machine circuitry, and I/O circuitry.

Exemplary device 100 further includes an atrial pulse generator 322 and a ventricular pulse generator 324 that generate pacing stimulation pulses for delivery by the right atrial lead 104, the coronary sinus lead 106, and/or the right ventricular lead 108 via an electrode configuration switch 326. The electrode configuration switch 326 may include multiple switches for connecting the desired electrodes to the appropriate I/O circuits, thereby providing complete electrode programmability. Accordingly, switch 326, in response to a control signal 327 from the microcontroller 320, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 322 and 324 may include dedicated, independent pulse generators, multiplexed pulse generators, or shared pulse generators. The pulse generators 322 and 324 are controlled by the microcontroller 320 via appropriate control signals 328 and 330, respectively, to trigger or inhibit the stimulation pulses.

Microcontroller 320 is illustrated as including timing control circuitry 332 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 320 may also implement an arrhythmia detector 334, a morphology detector 336, and an orthostatic compensator 338 comprising an exemplary diaphragm activator module 339. The orthostatic compensator 338 in turn can process input from physiological sensors 370, such as accelerometers and a blood pressure sensor 372, diagnose orthostatic hypotension incidents, and provide responsive therapies including diaphragm activation via the diaphragm activator module 339.

The diaphragm activator module 339 can stimulate the diaphragm directly and/or indirectly through its phrenic nerve stimulation sub-component (PN stim) 340. Stimulation therapies may compensate for detected OSH incidents using ongoing feedback from the physiological sensors 370. The orthostatic compensator 338 can also provide synergistic diaphragmatic and cardiac stimulation therapies as will be described in more detail below to further address OSH incidents.

The components 334, 336, and 338 may be implemented in hardware as part of the microcontroller 320, or as software/firmware instructions programmed into an implementation of the device 100 and executed on the microcontroller 320 during certain modes of operation. Although not shown, the microcontroller 320 may further include other dedicated circuitry and/or firmware/software components that assist in monitoring various conditions of the patient's heart and managing pacing therapies.

Atrial sensing circuits 344 and ventricular sensing circuits 346 may also be selectively coupled to the right atrial lead 104, coronary sinus lead 106, and the right ventricular lead 108, through the switch 326 to detect the presence of cardiac activity in each of the four chambers of the heart. The sensing circuits 344 and 346 may include dedicated sense amplifiers, multiplexed amplifiers, or shared amplifiers. Switch 326 determines the "sensing polarity" of the cardiac signal by selectively closing the appropriate switches. In this way, the clinician may program the sensing polarity independent of the stimulation polarity.

Each sensing circuit 344 and 346 may employ one or more low power precision amplifiers with programmable gain and/or automatic gain control, bandpass filtering, and a threshold detection circuit to selectively sense the cardiac signal of interest. The automatic gain control enables the exemplary device 100 to sense low amplitude signal characteristics of atrial or ventricular fibrillation.

The outputs of the atrial and ventricular sensing circuits 344 and 346 are connected to the microcontroller 320 which, in turn, is able to trigger or inhibit the atrial and ventricular pulse generators 322 and 324 in a demand fashion in response to the absence or presence of cardiac activity in the appropriate chambers of the heart. The sensing circuits 344 and 346 receive control signals from the microcontroller 320 over signal lines 348 and 350 to control, for example, the gain and/or threshold of polarization charge removal circuitry (not shown) and the timing of blocking circuitry (not shown) optionally coupled to the inputs of the sensing circuits 344, 346.

Cardiac signals are supplied to an analog-to-digital (A/D) data acquisition system 352, which is configured to acquire intracardiac electrogram signals, convert the raw analog data into a digital signal, and store the digital signals for later processing and/or telemetric transmission to an external device 354. The data acquisition system 352 is coupled to the right atrial lead 104, the coronary sinus lead 106, and the right ventricular lead 108 through the switch 326 to sample cardiac signals across any pair of desired electrodes.

The data acquisition system 352 is coupled to the microcontroller 320, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 320 detects a depolarization signal during a window following a stimulation pulse, the presence of which indicates that capture has occurred. The microcontroller 320 enables capture detection by triggering the ventricular pulse generator 324 to generate a stimulation pulse, starting a capture detection window using the timing control circuitry 332 within the microcontroller 320, and enabling the data acquisition system 352 via control signal 356 to sample the cardiac signal that falls in the capture detection window and, based on the amplitude, determines if capture has occurred.

The microcontroller 320 is further coupled to a memory 360 by a suitable data/address bus 362. The programmable operating parameters used by the microcontroller 320 are stored in memory 360 and used to customize the operation of the exemplary device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 360 through a telemetry circuit 364 in telemetric communication via a communication link 366 with the external device 354, such as a programmer, local transceiver, or a diagnostic system analyzer. The microcontroller 320 can activate the telemetry circuit 364 with a control signal 368. The telemetry circuit 364 allows intracardiac electrograms and status information relating to the operation of the exemplary device 100 (as contained in the microcontroller 320 or memory 360) to be sent to the external device 354 through the established communication link 366.

The physiological sensors 370 referred to above can further include, for example, "rate-responsive" sensors that adjust pacing stimulation rates according to the exercise state of the patient. Accordingly, the microcontroller 320 responds by adjusting the various pacing parameters (such as rate, AV Delay, V-V Delay, etc.) at which the atrial and ventricular pulse generators 322 and 324 generate stimulation pulses.

The physiological sensors 370 may include mechanisms and sensors to detect bodily movement, changes in cardiac output, changes in the physiological condition of the heart, diurnal changes in activity (e.g., detecting sleep and wake states), G-force acceleration of the pacemaker case 300, length of the cardiac QT interval, blood oxygen saturation, blood pH, changes in blood pressure, changes in temperature, respiration rate, and QRS wave duration. While shown as being included within the exemplary device 100, the physiological sensor(s) 370 may also be external to the exemplary device 100, yet still be implanted within or carried by the patient, e.g., a blood pressure probe. Examples of physiological sensors external to the case 300 that may be deployed by device 100 include sensors that, for example, sense respiration activities, $O_2$ saturation, evoked response, pH of blood, and so forth.

The illustrated physiological sensors 370 include one or more activity/position sensors 371 (e.g., 1D or 3D accelerometers, movement sensors, etc.) to detect changes in the patient's position. The activity/position sensors 371 can be used by the orthostatic compensator 338 to assist detection of orthostatic hypotension caused by transition from a less upright posture to a comparatively more upright posture. One example of postural change leading to orthostatic hypotension in susceptible individuals is a movement from a supine position in a rest state (e.g., sleeping in bed) to an upright position in a non-rest state (e.g., sitting or standing up). In some implementations, responsive to the detected postural change, the orthostatic compensator 338 may evaluate blood pressure to see if there has been a decrease in the blood pressure sustained for a duration that is longer than that which usually transpires before a normal intrinsic response (e.g., a baroreceptor reflex) intervenes. The orthostatic compensator 338 may then administer one or more diaphragm activation commands and/or pacing therapies to reduce the orthostatic hypotension. In other instances, the orthostatic compensator 338 may be configured to determine whether the sensed conditions are leading imminently to an OSH incident. In an affirmative scenario, the orthostatic compensator 338 may be capable of activating the diaphragm to reduce the OSH incident or avoid the OSH incident altogether.

In one configuration, accelerometer output signal from activity/position sensor 371 is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state. The activity variance can be monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995.

Other illustrated physiological sensors 370 include one or more blood pressure sensors 372, such as a photoplethysmograph (PPG) infrared light sensor surface mounted on the case 300 or external to the device 100. Thus, signals generated by the physiological sensors 370 can be passed to the microcontroller 320 for analysis by the orthostatic compensator 338. Such signals can be used to determine whether the patient is at rest, whether the patient is experiencing an episode of orthostatic hypotension or other cardiovascular disturbance, and whether to invoke any responsive therapy prescribed by the orthostatic compensator 338.

Still another of illustrated physiological sensors 370 is one or more phrenic nerve sensors 373. Direct measurement of phrenic nerve activity may be achieved using a cuff or other suitable electrode appropriately positioned in relationship to a phrenic nerve. For example, a cuff electrode substantially surrounding the right phrenic nerve in the thoracic cavity can detect signals indicative of intrinsic or native respiratory drive (at least to the right hemidiaphragm). Such signals are typically of amplitude measured in microvolts (e.g., less than approximately 30 microvolts). Sensing may be coordinated with other events, whether natural events or events related to some form of stimulation therapy. As discussed herein, some degree of synchronization may occur between calling for and/or delivering stimulation for diaphragm activation and sensing of native neural activity and/or other indicators of respiration and, in particular, exhalation.

The exemplary device 100 additionally includes a battery 376 that provides operating power to all of the components shown in FIG. 3. The battery 376 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 376 also desirably has predictable discharge characteristics so that elective replacement time can be detected. As one example, the exemplary device 100 employs lithium/silver vanadium oxide batteries.

The exemplary device 100 can further include magnet detection circuitry (not shown), coupled to the microcontroller 320, to detect when a magnet is placed over the exemplary device 100. A magnet may be used by a clinician to perform various test functions of the exemplary device 100 and/or to signal the microcontroller 320 that a wand of an external programmer (e.g., 354) is in place to receive or transmit data to the microcontroller 320 through the telemetry circuits 364.

The exemplary device 100 further includes an impedance measuring circuit 378 that is enabled by the microcontroller 320 via a control signal 380. The impedance measuring circuit 378 is used for many things, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 378 may be coupled to the switch 326 so that any desired electrode may be used.

The exemplary device 100 may be operated as an implantable cardioverter/defibrillator device, which detects the occurrence of an arrhythmia and automatically applies an appropriate electrical shock therapy to the heart aimed at terminating the detected arrhythmia. To this end, the microcontroller 320 further controls a shocking circuit 382 via a control signal 384. The shocking circuit 382 generates shocking pulses of low (e.g., up to 0.5 joules), moderate (e.g., 0.5-10 joules), or high energy (e.g., 11 to 40 joules), as selected by the microcontroller 320. Such shocking pulses are applied to the patient's heart 102 through at least two shocking electrodes selected, for example, from the left atrial coil electrode 126, the RV coil electrode 132, and/or the SVC coil electrode 134. As noted above, the case 300 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 320 is capable of controlling the synchronous or asynchronous delivery of the shocking pulses.

More generally, the exemplary device 100 can be programmed to stimulate different sets of cardiac muscles and non-cardiac tissues through the same lead/electrode system. The exemplary device 100 can be programmed to vary the output voltage of various pulses to effectively stimulate different muscles of the heart and phrenic nerve or diaphragm, even though the lead and electrode placement does not change.

Exemplary Methods

Figure 4:
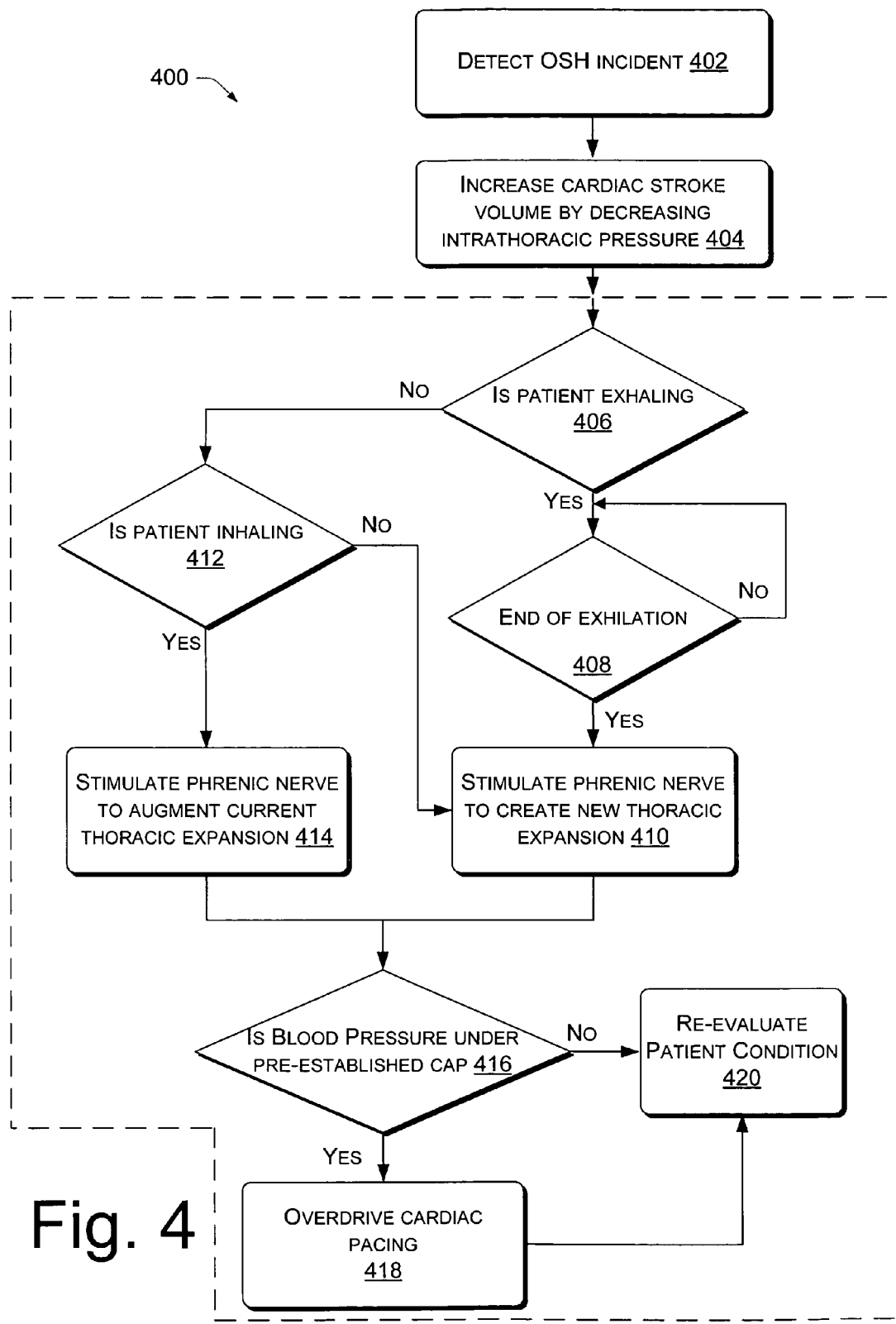
FIG. 4 is a flow diagram of an exemplary process for reducing orthostatic hypotension in accordance with one implementation.

FIG. 4 shows an exemplary process 400 for detecting conditions that might give rise to orthostatic hypotension and administering therapy at least to increase cardiac stroke volume and thereby reduce any effects of orthostatic hypotension. For instance, the process may stimulate the patient's phrenic nerve to increase cardiac stroke volume. This process 400 may be implemented in connection with any suitably configured device, although for purposes of explanation it will be described as being executed by the exemplary implantable device 100 described in relation to FIGS. 1-3.

In this flow diagram, various algorithmic acts are summarized in individual "blocks". Such blocks describe specific actions or decisions that are made or carried out as the process proceeds. Where a processor such as microcontroller 320 (or equivalent) is employed, the flow charts presented herein provide a basis for a "control program" or software/firmware that may be used by such a microcontroller (or equivalent) to effectuate the desired control of the stimulation device. As such, the process 300 is implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the concepts described herein include not only stimulation devices when programmed to perform the steps described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

At block 402, the process detects an OSH incident. As mentioned above, an OSH incident includes scenarios in which one or more sensed parameters indicate that the patient is undergoing OSH as well as scenarios in which the sensed parameter data indicate that the patient is about to experience OSH. For instance, various position sensors may indicate that the patient has just shifted from a generally horizontal or supine position to a generally vertical or upright position or that the patient is in the process of such a positional change which could lead to OSH. Rather than relying on a single set of parameters, the operation may verify or cross-check with additional parameters to increase the accuracy of any determination that the patient is undergoing an OSH incident. For instance, in relation to the above example, simultaneous to receiving the position change data, the process may receive blood pressure data indicting that the patient's blood pressure is dropping. Such a scenario is consistent with an OSH incident and may be more reliable that a single parameter. Examples of sensors suitable for obtaining data described in the above example are provided under the physiological sensors 370 description provided above in relation to FIG. 3.

At block 404, and responsive to detecting the OSH incident, the process 400 increases cardiac stroke volume by decreasing intra-thoracic pressure. Increased cardiac stroke volume can contribute to restoring normal blood pressure levels. Some implementations decrease intra-thoracic pressure through activation of the diaphragm. Diaphragm activation can be achieved at least by stimulating the patient's phrenic nerve. Examples of components and techniques suitable for phrenic nerve stimulation are described above in relation to FIGS. 1-3. An example of an exemplary process for achieving increased cardiac stroke volume and ultimately restored blood pressure through phrenic nerve stimulation is described in more detail below in relation to process blocks 406-420.

At block 406, the process 400 checks whether the patient is exhaling. If the patient is exhaling (i.e., the "Yes" branch from block 406), the process 400 waits for the end of exhalation, as indicated by block 408 with continuous loop formed by the "No" branch from block 408. Once the patient finishes exhaling (i.e., the "Yes" branch from block 408), the process 400 stimulates the patient's phrenic nerve to create new thoracic expansion (block 410). Such a process block can produce thoracic expansion between the patient's intrinsic inhalations and result in an additional breathe(s) between the patient's intrinsic or native breathes. Various examples and techniques of phrenic nerve stimulation are described above in relation to FIGS. 1-3.

With reference once again to block 406, if the patient is not exhaling (i.e., the "No" branch from block 406), the process 400 queries whether the patient is inhaling (block 412). If the patient is not inhaling (i.e., the "No" branch from block 412), the phrenic nerve is stimulated to instigate new thoracic expansion (block 410).

On the other hand, if the patient is inhaling (i.e., the "Yes" branch from block 412), the patient's phrenic nerve is stimulated to augment the patient's current or native thoracic expansion (block 414). This stimulation reduces intra-thoracic pressure and results in expanded cardiac volume. Collectively, process blocks 406-414 allow the phrenic nerve stimulation to be synchronized with the patient's native breathing. For instance, the process blocks avoid interfering with native breathing patterns such as may be encountered if phrenic nerve stimulation occurs while the patient is exhaling.

At block 416, after phrenic nerve stimulation at blocks 410 or 414, the process evaluates whether the patient's blood pressure is under a pre-established maximum value or cap. This operation serves to avoid over-compensating the patient's blood pressure to an undesirably high level. The pre-established maximum value may be a generically determined value or established on a patient-by-patient or situational basis. If the patient's blood pressure is under the pre-established value (i.e., the "Yes" branch from block 416), overdrive cardiac pacing is instigated (block 418). Overdrive cardiac pacing is characterized as increasing from a first basal pacing rate to a second faster pacing rate. For instance, assume that the patient's basal pacing rate is 60 cycles per second. Overdrive pacing may then raise the pacing rate to a higher rate of, for example, 80 cycles per minute. These are but examples provided for purposes of explanation and the skilled artisan should recognize other basal and overdrive pacing rates. Overdrive pacing augments phrenic nerve stimulation to achieve increased cardiac volume to increase the patient's blood pressure. Cardiac output volume equals cardiac stroke volume multiplied by the stroke rate. Phrenic nerve stimulation serves to increase cardiac stroke volume and overdrive pacing serves to increase the stroke rate.

Blocks 416-418 provide one example for achieving a desired functionality of returning the patient to a normal blood pressure level. There are other examples. For instance, another exemplary process may utilize a three tiered approach such that if the patient's blood pressure is below a value x, the process continues phrenic nerve stimulation and instigates overdrive pacing; and if the value is between the value x and a higher value y, the process continue phrenic nerve stimulation but does not instigate overdrive pacing; and finally, if the value is greater than the value y, the process stops phrenic stimulation. Suitable values for x and y could be based on systolic values of 110 and 130, respectively. This is but one example, and such values may be established on a patient-by-patient basis.

If the patient's blood pressure is over the pre-established value (i.e., the "No" branch from block 416), or at some point after overdrive cardiac pacing is instigated at block 418, the process re-evaluates the patient's physiological parameters (block 420). For instance, the physiological data may indicate that the OSH incident has ended, normal blood pressure has been restored, and that the patient is generally stationary. In such a scenario, cardiac pacing may be restored to the basal rate and phrenic nerve stimulation ceased. Of course, the changes to the pacing rate and/or the phrenic stimulation may be implemented incrementally while continuing to monitor the patient's physiological conditions to avoid causing any sudden large variance in the patient's blood pressure or other physiological conditions.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   detecting an orthostatic hypotension incident in a patient;
   responsive to said detecting, increasing cardiac stroke volume at least in part by stimulating the patient's phrenic nerve; and
   responsive to said stimulating, measuring the patient's blood pressure and adjusting subsequent stimulating, based at least in part, upon the measured blood pressure.

2. The method of claim 1, wherein the stimulating comprises delivering an electrical stimulation to the phrenic nerve via at least one cuff positioned around the phrenic nerve.

3. The method of claim 2, wherein the electrical stimulation is delivered to a portion of the phrenic nerve associated with a respiratory diaphragm of the patient.

4. The method of claim 1, wherein the stimulating comprises:
   determining if the patient is exhaling; and,
   in an instance where the patient is not exhaling, delivering an electrical stimulation to the phrenic nerve.

5. The method of claim 1, wherein the stimulating comprises:
   determining whether the patient is exhaling;
   in an instance where the patient is not exhaling, ascertaining if the patient is inhaling;
   in an instance where the patient is inhaling, stimulating the phrenic nerve sufficiently to augment thoracic expansion; and,
   in an instance where the patient is not inhaling, stimulating the phrenic nerve sufficiently to cause thoracic expansion.

6. The method of claim 1 further comprising, prior to said stimulating, checking for intrinsic neural stimulation of the phrenic nerve.

7. The method of claim 1 further comprising adjusting cardiac pacing from a first cardiac pacing rate to a second cardiac pacing rate that is higher than the first cardiac pacing rate.

8. A method comprising:
- detecting a patient condition indicative of at least one of orthostatic hypotension or impending orthostatic hypotension;
- responsive to said detecting, increasing cardiac stroke volume at least in part by stimulating diaphragm activation; and
- responsive to said stimulating, measuring the patient's blood pressure and adjusting subsequent stimulating, based at least in part, upon the measured blood pressure.

9. The method of claim 8, wherein said stimulating comprises stimulating a phrenic nerve of the patient.

10. The method of claim 9, wherein said stimulating a phrenic nerve of the patient is accomplished with a lead which also contributes to cardiac stimulation.

11. The method of claim 8, wherein said detecting comprises detecting and evaluating at least two parameters relating to positional data, acceleration data, or blood pressure data.

12. The method of claim 8 further comprising increasing cardiac stimulation from a first cardiac pacing rate to a higher second cardiac pacing rate concurrently with said stimulating.

13. An implantable device, comprising:
- at least one pulse generator to produce electrical stimulation;
- an orthostatic compensator configured to receive input from sensors and diagnose an orthostatic hypotension (OSH) incident;
- a phrenic stimulator to coordinate electrical stimulation to a phrenic nerve to treat the OSH incident; and
- a pressure sensor to measure the patient's blood pressure in response to the electrical stimulation to the phrenic nerve and to adjust subsequent electrical stimulation to the phrenic nerve, based at least in part, upon the measured blood pressure.

14. The implantable device of claim 13, wherein the phrenic stimulator is configured to stimulate a portion of the phrenic nerve associated with a patient's respiratory diaphragm.

15. The implantable device of claim 13, wherein the phrenic stimulator is configured to avoid stimulating the phrenic nerve during native stimulation of the phrenic nerve by the patient's central nervous system.

16. The implantable device of claim 13, wherein the phrenic stimulator is configured to avoid stimulating the phrenic nerve while the patient is exhaling.

17. The implantable device of claim 13, wherein the phrenic stimulator is configured to stimulate the phrenic nerve during a first period of patient inhalation and second period between patient exhalation and a following native inhalation to decrease intra-thoracic pressure.

18. The implantable device of claim 13, wherein the orthostatic compensator is configured to increase cardiac stimulation from a first cardiac pacing rate to a higher second cardiac pacing rate concurrently with stimulation of the phrenic nerve.

\* \* \* \* \*